(12) United States Patent
Pelzer et al.

(10) Patent No.: US 8,790,900 B2
(45) Date of Patent: Jul. 29, 2014

(54) MICROORGANISMS HAVING ENHANCED SUCROSE MUTASE ACTIVITY

(75) Inventors: Stefan Pelzer, Pfungstadt (DE); Christian Zurek, Lorsch (DE); Thomas Rose, Worms (DE); Jürgen Eck, Bensheim (DE); Wolfgang Wach, Worms (DE); Michael Klingeberg, Grünstadt (DE); Karsten Harms, Worms (DE)

(73) Assignee: Südzucker Aktiengesellschaft Mannheim/Ochsenfurt, Mannheim (DE)

( * ) Notice: Subject to any disclaimer, the term of this patent is extended or adjusted under 35 U.S.C. 154(b) by 28 days.

(21) Appl. No.: 13/509,250

(22) PCT Filed: Oct. 23, 2010

(86) PCT No.: PCT/EP2010/006487
§ 371 (c)(1),
(2), (4) Date: May 10, 2012

(87) PCT Pub. No.: WO2011/057710
PCT Pub. Date: May 19, 2011

(65) Prior Publication Data
US 2012/0225458 A1 Sep. 6, 2012

(30) Foreign Application Priority Data
Nov. 11, 2009 (DE) .......................... 10 2009 053 566

(51) Int. Cl.
C12P 19/24 (2006.01)
C12N 1/20 (2006.01)
C12N 15/00 (2006.01)
C12N 15/74 (2006.01)
C12P 19/34 (2006.01)
C07H 21/04 (2006.01)

(52) U.S. Cl.
USPC ..................... 435/94; 435/252.3; 435/252.33; 435/252.34; 435/471; 435/91.1; 536/24.1

(58) Field of Classification Search
USPC ........... 435/94, 252.3, 252.33, 252.34, 320.1, 435/471, 91.1; 536/24.1
See application file for complete search history.

(56) References Cited

U.S. PATENT DOCUMENTS 5,786,140 A * 7/1998 Mattes et al. .................. 435/134
7,250,282 B2 * 7/2007 Birch et al. ................... 435/233
2003/0203468 A1 10/2003 Mattes et al.

FOREIGN PATENT DOCUMENTS

CA 1110189 A 10/1981
CA 2 150 928 C 2/2005
DE 693 28 442 T2 9/2000
EP 0 001 099 B1 9/1978
WO WO 2009/152480 A2 12/2009

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
International Search Report from PCT/EP2010/006487, dated Jun. 30, 2011 (7 pages; English Translation).
Database Accession No. AXU25741; "*S. enterica* 3,4 dihydroxy-2-butanone-4-phosphate synthase promoter"; Mar. 4, 2010 (2 pages).
GenBank Accession No. CP000826.1; "*Serratia proteamaculans* 568, complete genome"; Feb. 22, 2008 (2 pages).
GenBank Accession No. CP000826.1 sequence comparison with SEQ ID No. 2. NCBI Blast:Nucleotide Sequence. Retrieved from the internet at blast.ncbi.nlm.nih.gov/Blast.cgi on Jul. 13, 2010 (1 page).
Alper et al. "Tuning genetic controls through promoter engineering"; *Proc. Nat. Acad. Sci. USA*; 102(36):12678-12683 (Sep. 2005).
Cha et al.; "Molecular cloning and functional characterization of a sucrose isomerase (isomaltuose synthase) gene from *Enterobacter* sp FMB-1"; *J. Appl. Microbiol.*; 107(4):1119-1130 (Oct. 2009).
De Oliva-Neto et al.; "Isomaltulose production from sucrose by *Protaminobacter rubrum* immobilized in calcium alginate"; *Bioresource Technology*; 100:4252-4256 (Sep. 2009).
Herrero et al.; "Transposon Vectors Containing Non-Antibiotic Resistance Selection Markers for Cloning and Stable Chromosomal Insertion of Foreign Genes in Gram-Negative Bacteria"; *J. Bacteriol.*; 172(11):6557-6567 (Nov. 1990).
McCleary, William R.; "Application of promoter swapping techniques to control expression of chromosomal genes"; *Appl. Microbiol. and Biotechnol.*; 84:641-648 (2009).
Richter et al.; "Biosynthesis of Riboflavin: Cloning, Sequencing, and Expression of the Gene Coding for 3,4-Dihydroxy-2-Butanone 4-Phosphate Synthase of *Escherichia coli*"; *J. Bacteriol.*; 174(12):4050-4056 (1992).
Sawitzke et al; "Recombineering: In vivo genetic engineering in *E. coli*, *S. enterica*, and Beyond"; *Meth. Enzymol.*; 421:171-199 (Jan. 2007).

* cited by examiner

*Primary Examiner* — Ganapathirama Raghu
(74) *Attorney, Agent, or Firm* — Kilpatrick Townsend & Stockton LLP

(57) ABSTRACT

The invention relates to the biotechnological production of isomaltulose and isomaltulose-containing compositions and improved means, therefore particularly microbial cells.

14 Claims, 6 Drawing Sheets

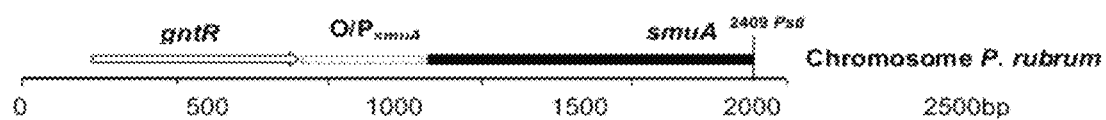
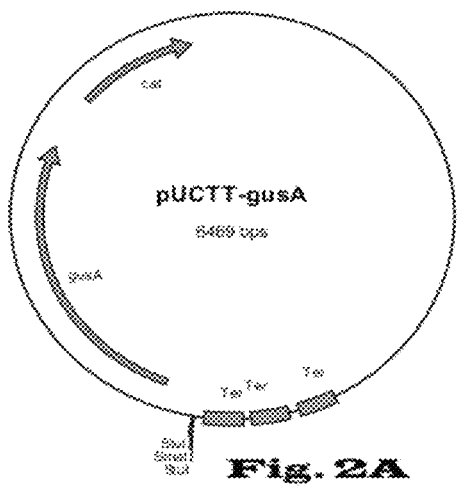
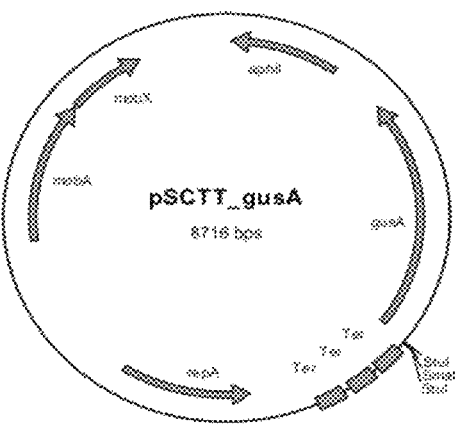
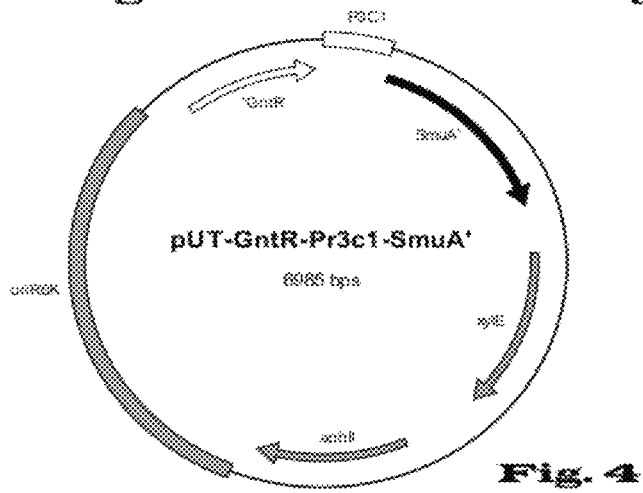

SEQUENCE LISTING

```
<160> NUMBER OF SEQ ID NOS: 30

<210> SEQ ID NO 1
<211> LENGTH: 2409
<212> TYPE: DNA
<213> ORGANISM: Protaminobacter rubrum

<400> SEQUENCE: 1
ttttccattc aaagagtagg gactttgaaa aaaaaggtcg caaaactatt aatcattttg      60
tgatcgcatt catgttttct ccttcggtga agtggtctac ttttatggcg atttgtatac     120
attaaagtga tcaaggaaaa aatagccaga ggaatagcca aataaatttc aggttttaca     180
gtgcggtaac ctcttttgt tgcgcggtta tcaggattca tttagggata aagaggtctt      240
caagtgatct acaaaacgct tgctgaacgt ctgagaatac gtatcaattc tgctgatttt     300
gctatcggcg atgctttacc cagtgagaaa cgtctggctg ccgaatttc tgtatcgagg      360 atgacactcc gcaaagcggt aaatttactg attgaatggg ggctggtacg tcgctgtcac     420
ggcagcggaa ccttcgtcgc gcagaaagat ctccaacatg aaactcgtgg gctgatgggg     480
ttttcagaac tgatgaaaga actgggccgc cccacggtga gcgaggtgct ggagtttcga     540
atgatgggag ccccccagc catcgccagc cagctgcgaa tcaaggccga tgaacgcatt      600
tactattcgc gtcgcgtaag gtttgtggaa gggaagcctg tggtgctgga agatagttac     660
atgcctggca ggttatttgg caacctttca gtcgcacatc tggagggttc aaagtttttcg    720 tatatagaag acgaatgcca tatcaatatc gcagggaatt acgaaagctt cagcccgatc     780
ttggcagaca gcacgatcgg cgcgctactg cacgttgccg aaggcacgcc gctgctgcgc     840
ctgacatcgc tttcttacag tgataccggc gactatatca actattcggt gatattcaga     900
aatgccaatg aataccacgt ggactaccat ttgaagagga ataaatagcg ggcgaagggg     960
agctacattc ctactatata gcaattgcaa taattcccag tctaatcatc acgttgatca    1020
acggaatttc ccgcaagata acatgaaaat gttttttgtt atcgcaaatt aatagtggtt    1080
tagagcgttc gcagccctct tgctaacacg gtttagcaag gtatgctaaa aaacagctga    1140
tttaaaacga atgtcactta aaaaatgtca atgctttata tttactttac ccagtcattg    1200
ttcgggaaca taattgaaaa gcttctatta gatactgaaa attaatcagt attaaattaa    1260
taaattaacg attaaatatt taaatgtcag gggaaacatt gaattaggtt tattttttcga   1320 ataagaaaca ggagagtatt gtaatgcccc gtcaaggatt gaaaactgca ctagcgattt    1380
```

```
ttctaaccac atcattatgc atctcatgcc agcaagcctt cggtacgcaa caacccttgc    1440
ttaacgaaaa gagtatcgaa cagtcgaaaa ccatacctaa atggtggaag gaggctgttt    1500
tttatcaggt gtatccgcgc tcctttaaag acaccaacgg agatggcatc ggggatatta    1560
acggcatcat agaaaaatta gactatctaa aagccttggg gattgatgcc atttggatca    1620
acccacatta tgattctccg aacacggata atggttacga tatcgtgat tatcgaaaaa      1680 tcatgaaaga atatggcacg atggaggatt tgaccgcct gatttctgaa atgaaaaaac      1740
ggaatatgcg gttgatgatt gatgtggtca tcaaccacac cagcgatcaa aacgaatggt    1800
ttgttaaaag taaagcagt aaggataatc cttatcgcgg ctattatttc tggaaagatg      1860
ctaaagaagg gcaggcgcct aataattacc cttcattctt tggtggctcg gcgtggcaaa    1920
aagatgaaaa gaccaatcaa tactacctgc actattttgc taaacaacag cctgacctaa    1980
actgggataa tcccaaagtc cgtcaagatc tttatgcaat gttacgtttc tggttagata    2040
aaggcgtgtc tggtttacgt tttgatacgg tagcgaccta ctcaaaaatt ccggatttcc    2100
caaatctcac ccaacaacag ctgaagaatt ttgcagcgga gtataccaag ggccctaata    2160
ttcatcgtta cgtcaatgaa atgaataaag aggtcttgtc tcattacgac attgcgactg    2220
ccggtgaaat ctttggcgta cccttggatc aatcgataaa gttcttcgat cgccgccgtg    2280
atgagctgaa cattgcattt acctttgact taatcagact cgatcgagac tctgatcaaa    2340
gatggcgtcg aaaagattgg aaattgtcgc aattccggca gatcatcgat aacgttgacc    2400
gtactgcag                                                            2409

<210> SEQ ID NO 2
<211> LENGTH: 321
<212> TYPE: DNA
<213> ORGANISM: Protaminobacter rubrum

<400> SEQUENCE: 2
ctgttgccta gtgtaatgcg agttgcccgc cggataaacc aataaccgca ttctccgcag      60
ggggccgaat tgtgcttttg ccaattgccc tgattaatca ttagcgttat agtcagaatg     120
cttattctca gggcggggtg caagtcccca ccggcggtaa atcaccttct acggtgaaag     180
cccgcgagcg ctcagccagt ctcttgtagt ttggttagag gtcagcagat ccggtgtaat     240
tccggggccg acggttatag tccgatgggg agagagtaac ggtatctgcc gggcttgcgc     300
ccgcttgcgt tattttttta g                                              321

<210> SEQ ID NO 3
<211> LENGTH: 313
<212> TYPE: DNA
<213> ORGANISM: Serratia proteamaculans

<400> SEQUENCE: 3
ctgtcgccta gtgtaatgcg agttgcccgc cggataaact atttaaccgc attccctgcg      60
gctggccgaa ttgtgctttt gccaattgcc ctgattaatc attagcgtta tagtcgagag     120
gcttattctc agggcggggt gcaagtcccc accggcggta atcaccttc tacggtgaaa      180 gcccgcgagc gctcagccag tctcttgcag tttggttaga ggtcagcaga tccggtgtaa    240
ttccggggcc gacggttata gtccggatgg gagagagtaa cggtatctgc cgggtttgcg    300
cccgcttgcg tta                                                       313

<210> SEQ ID NO 4
<211> LENGTH: 228
```

```
<212> TYPE: DNA
<213> ORGANISM: Protaminobacter rubrum

<400> SEQUENCE: 4
tcttaccggt tagtgttagt aaatatgtac gattctgcgt ttttttttag agctttatca      60
catcacactt gtaactttcg cgccacgttg tagactttac atcgccaagg ttgctctata     120
acgccagaaa aactggccga gtaacaaacg agggctcaaa ccttggcgaa ggaatttaac     180
caagggctta aaacagcttt aaagctcatt gcctatttgg atgataac                  228

<210> SEQ ID NO 5
<211> LENGTH: 180
<212> TYPE: DNA
<213> ORGANISM: Serratia proteamaculans

<400> SEQUENCE: 5
agagctttat cacatcacac ttgtaacttt cgcgccacgt tgtagacttt acatcgccaa      60
ggttgctcta taacgccaga taaactggca gagtaacaaa cgagggctca aaccttggcg     120
aaggaattta accaagggct aaaacagctt ttaaagctca ttgcctattt ggatgataac     180

<210> SEQ ID NO 6
<211> LENGTH: 178
<212> TYPE: DNA
<213> ORGANISM: Serratia marcescens

<400> SEQUENCE: 6
agagccttat cacatcacac ttgtaacttt cgcgccacgt tgtagacttt acatcgccaa      60
ggttgctcta taacgtcaga aaaatcggcg agtaacaaac gagggcttaa accttggcga     120
aggaatttaa ccaagggctt aaacagcttt aaagctcatt gcctatttgg atgataac      178

<210> SEQ ID NO 7
<211> LENGTH: 109
<212> TYPE: DNA
<213> ORGANISM: Protaminobacter rubrum

<400> SEQUENCE: 7
gttttttgcc tctctagaat taggggattg agcgtgtggc cactttatgg tgtacatgtt      60
aatcttgcaa gaacacacca aaaagtaagt aacacccaaa aggtaagt                 109

<210> SEQ ID NO 8
<211> LENGTH: 59
<212> TYPE: DNA
<213> ORGANISM: Erwinia carotovora

<400> SEQUENCE: 8
tgtacaggtt aatgtaacaa gaacacacca ataagtgggt aacaccctaa aggtaagt       59

<210> SEQ ID NO 9
<211> LENGTH: 209
<212> TYPE: DNA
<213> ORGANISM: Protaminobacter rubrum

<400> SEQUENCE: 9
ggtttgaacg ttgcgatttc ttccacagtt aaggaaaagt caccttgcta taacggtatc      60
agcagtggaa taatgcgttt actttccacg ttgattctcg ttaaacaggg aaaacggtgg     120
gattataaaa tttgtctgat ggcgcaaaaa cgcagcaatg gcgtaagacg taatgcgaaa     180
tcaaacaatt agcgggctgc gggttgcag                                      209
```

<210> SEQ ID NO 10
<211> LENGTH: 210
<212> TYPE: DNA
<213> ORGANISM: Serratia proteamaculans

<400> SEQUENCE: 10

```
ggtttgaacg tttgcgattt cttccgcagt taaggaaaag tcaccttgct ataacagtat      60
cagcagtgga ataatgcgtt tactttccac gttgattctc gttaaacagg gaaaactgtg     120
gaattataaa atttgtctga tggcacaaaa acgcagcaat ggcgtaagac gtaatgtgaa     180
atcaaacaat tagcgggctg cgggttgcag                                      210
```

<210> SEQ ID NO 11
<211> LENGTH: 165
<212> TYPE: DNA
<213> ORGANISM: Serratia marcescens

<400> SEQUENCE: 11

```
ttgctataac ggcatcagca gtggaataat gcagtcactt tccgcgttga ttctcgttaa      60
acagggaaaa cggtggaatt ataaaatttg tctgatcgcg caaaaacgca gcaatggcgt     120
aagacgtaat gcgaaatcaa acaattagcg ggctgcgggt tgcag                     165
```

<210> SEQ ID NO 12
<211> LENGTH: 242
<212> TYPE: DNA
<213> ORGANISM: Protaminobacter rubrum

<400> SEQUENCE: 12

```
tgtgtttctc ttcaccgcgt tgagatcgct gctcacatcg gtacatggcg gtaactgtcc      60
tcctgattgt acttgaaaaa cggctcagat aaacgccatg aaagaaactg tgcttttttt     120 cttcttttt ctgcttctgg tcttattctg ctcttgtcat atgcgggatt attgcgtaga     180
attcgcgccc tattgtgaat atttatagcg cgctctgtac taaacagttg ggcacgcgga     240
aa                                                                    242
```

<210> SEQ ID NO 13
<211> LENGTH: 242
<212> TYPE: DNA
<213> ORGANISM: Serratia proteamaculans

<400> SEQUENCE: 13

```
tgtgtttctc ttcaccgcgt tgagatcgct gctcacatcg gtacatggcg gtaactgtcc      60
ctctgattgt acttgaaaaa cggcccagat aaacgccatg aaagaaactg tgcttttttt     120 cttcttttt ctgcttctgg tcttattctg ctcttgtcat acgctggatt attgcgtaga     180
attcgcgccc tattgtgaat atttatagcg cgctctgtac tgaacagttg ggcacgcgga     240
aa                                                                    242
```

<210> SEQ ID NO 14
<211> LENGTH: 120
<212> TYPE: DNA
<213> ORGANISM: Protaminobacter rumbrum

<400> SEQUENCE: 14

```
ccgattttt cacttttat cggtttatg tgatccaggt tgtggacaaa atccggtcta      60
attgctgtac tgtactggac acaggttcag tgtcttacat tcacgttaaa ggtaagtttg     120
```

<210> SEQ ID NO 15
<211> LENGTH: 118
<212> TYPE: DNA
<213> ORGANISM: Serratia proteamaculans

<400> SEQUENCE: 15

```
gatttttca ctctttatcg attttatgtg atccaggttg tggacaaaat cccgtctaat      60
tgctgtactg tattggacac atgtttagtg tctttcattc acgttaaagg taagtttg      118
```

<210> SEQ ID NO 16
<211> LENGTH: 115
<212> TYPE: DNA
<213> ORGANISM: Yersinia pseudotuberculosis

<400> SEQUENCE: 16

```
tttttcactt tttctctctt ttttgtgatc tccattgtgg acaaaaaacg gttctattgc      60
tgtactgtaa ttgacacaat ttttgtgtcc aacattcacg ttaaaggtaa gtttg            115
```

<210> SEQ ID NO 17
<211> LENGTH: 238
<212> TYPE: DNA
<213> ORGANISM: Protaminobacter rubrum

<400> SEQUENCE: 17

```
gcgattttt cgcgatcctt cggggatctt tagctgttcg ggacttgagc acttacgcct      60
cagagcgtat actacgccac ctttgagaat ctttgggtttg gcgtaagagc ctatctcagc    120
aggtttctaa cctgatgtgt ggtttctgac ctgatgacgg gagtctcctc agtatggagt    180
ttgctgagat gggctctaaa agcctgacga ggcggccata ccctatacga agctcgag      238
```

<210> SEQ ID NO 18
<211> LENGTH: 238
<212> TYPE: DNA
<213> ORGANISM: Serratia proteamaculans

<400> SEQUENCE: 18

```
gcgattttt cgcgatcctt ctgggatctt tagctgttcg ggacttgagc acttacgctt      60
cagagcgtat actacgccac ctttgagaat ctttgggtttg gcgtaagagc ctatctcagc    120
aggtttccaa cctgatgtgt ggtttctaac ctgatgacga gagtctcctc agtatgaagt    180
ttgctgagat gggctctaaa agcctgacga ggcggccata ctctatacga agctcgag      238
```

<210> SEQ ID NO 19
<211> LENGTH: 237
<212> TYPE: DNA
<213> ORGANISM: Serratia marcescens

<400> SEQUENCE: 19

```
gcgattttt cgcgatcttt gtgggatctt tagctgatcg ggaattgagc acttacgctt      60
cagagcgtat actacgccac ctttgagaat ctttgggtttg gcgcaagagc ctatctcagc    120
aggtttgtga cctgatgtgt ggtttctacc tgatgacgag agtctcctca gtatgaagtt    180
tgctgagatg ggctctaaaa gcctgacgag gcggccatac cctatacgaa gctcgag       237
```

<210> SEQ ID NO 20
<211> LENGTH: 152
<212> TYPE: DNA
<213> ORGANISM: Serratia proteamaculans

<400> SEQUENCE: 20

```
gggttaaccg ctttttttct gtcttcatct tcttcgactt taggctgctt tggagtaatg    60
gatacgcatt taagatatca cttgatattt taaatgcacc ccactaaatt aagatatcat   120
atgaactttg aaactcactt aagattttaa tg                                 152
```

<210> SEQ ID NO 21
<211> LENGTH: 86
<212> TYPE: DNA
<213> ORGANISM: Serratia proteamaculans

<400> SEQUENCE: 21

```
gcattcaaga tatcacttga tattttaaac ctctaccact agatttggat atcacttgaa    60
ctttgaaatt cacttaagat tttaat                                         86
```

<210> SEQ ID NO 22
<211> LENGTH: 630
<212> TYPE: DNA
<213> ORGANISM: Protaminobacter rubrum

<400> SEQUENCE: 22

```
gcgcctgaca tcgctttctt acagtgatac cggcgactat atcaactatt cggtgatatt    60
cagaaatgcc aatgaatacc acgtggacta ccatttgaag aggaataaat agcgggcgaa   120
ggggagctac attcctacta tatagcaatt gcaataattc ccagtctaat catcacgttg   180
atcaacggaa tttcccgcaa gataacatga aaatgttttt tgttatcgca attaatagt    240 ggtttagagc gttcgcagcc ctcttgctaa cacggtttag caaggtatgc taaaaaacag   300
ctgatttaaa acgaatgtca cttaaaaaat gtcaatgctt tatatttact ttacccagtc   360
attgttcggg aacataattg aaaagcttct attagatact gaaaattaat cagtattaaa   420
ttaataaatt aacgattaaa tatttaaatg tcagggaaaa cattgaatta ggtttatttt   480
tcgaataaga aacaggagag tattgtaatg ccccgtcaag gattgaaaac tgcactagcg   540
atttttctaa ccacatcatt atgcatctca tgccagcaag ccttcggtac gcaacaaccc   600
ttgcttaacg aaaagagtat cgaacagtcg                                    630
```

<210> SEQ ID NO 23
<211> LENGTH: 37
<212> TYPE: PRT
<213> ORGANISM: Protaminobacter rubrum

<400> SEQUENCE: 23

```
Leu Arg Leu Thr Ser Leu Ser Tyr Ser Asp Thr Gly Asp Tyr Ile Asn
  1               5                  10                  15

Tyr Ser Val Ile Phe Arg Asn Ala Asn Glu Tyr His Val Asp Tyr His
                 20                  25                  30

Leu Lys Arg Asn Lys
             35
```

<210> SEQ ID NO 24
<211> LENGTH: 41
<212> TYPE: PRT
<213> ORGANISM: Protaminobacter rubrum

<400> SEQUENCE: 24

```
Met Pro Arg Gln Gly Leu Lys Thr Ala Leu Ala Ile Phe Leu Thr Thr
  1               5                  10                  15

Ser Leu Cys Ile Ser Cys Gln Gln Ala Phe Gly Thr Gln Gln Pro Leu
                 20                  25                  30
```

Leu Asn Glu Lys Ser Ile Glu Gln Ser
         35                  40

<210> SEQ ID NO 25
<211> LENGTH: 520
<212> TYPE: DNA
<213> ORGANISM: Protaminobacter rubrum

<400> SEQUENCE: 25
catctggagg gttcaaagtt ttcgtatata gaagacgaat gccatatcaa tatcgcaggg     60
aattacgaaa gcttcagccc gatcttggca gacagcacga tcggcgcgct actgcacgtt    120
gccgaaggca cgccgctgct gcgcctgaca tcgctttctt acagtgatac cggcgactat    180
atcaactatt cggtgatatt cagaaatgcc aatgaatacc acgtggacta ccatttgaag    240
aggaataaat agcgggcgaa ggggagctac attcctacta tatagcaatt gcaataattc    300
ccagtctaat catcacgttg atcaacggaa tttcccgcaa gataacatga aaatgtttaa    360
acaggagagt attgtaatgc cccgtcaagg attgaaaact gcactagcga ttttttctaac   420 cacatcatta tgcatctcat gccagcaagc cttcggtacg caacaaccct tgcttaacga    480
aaagagtatc gaacagtcga aaccatacc taaatggtgg                          520

<210> SEQ ID NO 26
<211> LENGTH: 83
<212> TYPE: PRT
<213> ORGANISM: Protaminobacter rubrum

<400> SEQUENCE: 26

His Leu Glu Gly Ser Lys Phe Ser Tyr Ile Glu Asp Glu Cys His Ile
  1               5                  10                  15

Asn Ile Ala Gly Asn Tyr Glu Ser Phe Ser Pro Ile Leu Ala Asp Ser
             20                  25                  30

Thr Ile Gly Ala Leu Leu His Val Ala Glu Gly Thr Pro Leu Leu Arg
         35                  40                  45

Leu Thr Ser Leu Ser Tyr Ser Asp Thr Gly Asp Tyr Ile Asn Tyr Ser
     50                  55                  60

Val Ile Phe Arg Asn Ala Asn Glu Tyr His Val Asp Tyr His Leu Lys
 65                  70                  75                  80

Arg Asn Lys

<210> SEQ ID NO 27
<211> LENGTH: 48
<212> TYPE: PRT
<213> ORGANISM: Protaminobacter rubrum

<400> SEQUENCE: 27

Met Pro Arg Gln Gly Leu Lys Thr Ala Leu Ala Ile Phe Leu Thr Thr
  1               5                  10                  15

Ser Leu Cys Ile Ser Cys Gln Gln Ala Phe Gly Thr Gln Gln Pro Leu
             20                  25                  30

Leu Asn Glu Lys Ser Ile Glu Gln Ser Lys Thr Ile Pro Lys Trp Trp
         35                  40                  45

<210> SEQ ID NO 28
<211> LENGTH: 780
<212> TYPE: DNA
<213> ORGANISM: Protaminobacter rubrum

<400> SEQUENCE: 28

```
ttcaaagttt tcgtatatag aagacgaatg ccatatcaat atcgcaggga attacgaaag    60
cttcagcccg atcttggcag acagcacgat cggcgcgcta ctgcacgttg ccgaaggcac   120
gccgctgctg cgcctgacat cgctttctta cagtgatacc ggcgactata tcaactattc   180
ggtgatattc agaaatgcca atgaatacca cgtggactac catttgaaga ggaataaata   240
gcgggcgaag gggagctaca ttcctactat atagcaattc tgttgcctag tgtaatgcga   300
gttgcccgcc ggataaacca ataaccgcat tctccgcagg gggccgaatt gtgcttttgc   360
caattgccct gattaatcat tagcgttata gtcagaatgc ttattctcag ggcggggtgc   420
aagtccccac cggcggtaaa tcaccttcta cggtgaaagc ccgcgagcgc tcagccagtc   480
tcttgtagtt tggttagagg tcagcagatc cggtgtaatt ccggggccga cggttatagt   540
ccggatggga gagagtaacg gtatctgccg ggcttgcgcc cgcttgcgtt attttttag    600 aaacaggaga gtattgtaat gccccgtcaa ggattgaaaa ctgcactagc gattttctca   660
accacatcat tatgcatctc atgccagcaa gccttcggta cgcaacaacc cttgcttaac   720
gaaaagagta tcgaacagtc gaaaaccata cctaaatggt ggaaggaggc tgttttttat   780
```

```
<210> SEQ ID NO 29
<211> LENGTH: 80
<212> TYPE: PRT
<213> ORGANISM: Protaminobacter rubrum

<400> SEQUENCE: 29
```

Gly Ser Lys Phe Ser Tyr Ile Glu Asp Glu Cys His Ile Asn Ile Ala
1               5                   10                  15

Gly Asn Tyr Glu Ser Phe Ser Pro Ile Leu Ala Asp Ser Thr Ile Gly
            20                  25                  30

Ala Leu Leu His Val Ala Glu Gly Thr Pro Leu Leu Arg Leu Thr Ser
        35                  40                  45

Leu Ser Tyr Ser Asp Thr Gly Asp Tyr Ile Asn Tyr Ser Val Ile Phe
    50                  55                  60

Arg Asn Ala Asn Glu Tyr His Val Asp Tyr His Leu Lys Arg Asn Lys
65                  70                  75                  80

```
<210> SEQ ID NO 30
<211> LENGTH: 54
<212> TYPE: PRT
<213> ORGANISM: Protaminobacter rubrum

<400> SEQUENCE: 30
```

Met Pro Arg Gln Gly Leu Lys Thr Ala Leu Ala Ile Phe Leu Thr Thr
1               5                   10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr
    50

MICROORGANISMS HAVING ENHANCED SUCROSE MUTASE ACTIVITY

CROSS REFERENCE TO RELATED APPLICATIONS

The present application is a U.S. National Phase of PCT/EP2010/006487, filed Oct. 23, 2010, which claims benefit of German Application Number 10 2009 053 566.7, filed Nov. 11, 2009, the contents of each are incorporated by reference herein in their entirety.

BRIEF DESCRIPTION OF THE DRAWINGS

FIG. 1 illustrates the chromosomal organization up-stream in reference to the smuA-gene with regulatory sequences in the 5'-UTR (promoter, operator); SEQ ID NO: 1: In this region an "open reading frame" (ORF) of 234 amino acids could be identified. It shows significant homologies to the so-called GntR-Type transcription-regulators; in the following, the respective gene is called gntR. An approximately 400 bp comprising inter-genetic region is located between gntR and smuA, comprising regulatory elements (promoter, operator) of the smuA-expression (also see FIG. 3A).

FIG. 2 shows as an example vector cards of the vectors that can be used according to the invention "high-copy"-plasmid pUCTT-gusA (FIG. 2A) and "low-copy"-plasmid pSCTT-gusA (FIG. 2B) for the production of P. rubrum promoter gene banks Preferably the α-glucuronidase gene gusA was used as the promoter reporter gene. Preferably the substitute sequences SEQ ID NO: 2 through SEQ ID NO: 11 (Table 1A) were used in connection with the plasmid according to FIG. 2A; the substitute sequences SEQ ID NO: 12 through SEQ ID NO: 21 (Table 1B) were used in connection with the plasmid according to FIG. 2B.

FIG. 4 shows an example of a vector map of the preferred promoter substitute plasmid pUT-GntR-Pr3C1-SmuA produced in the context of the invention, comprising the substitute sequence according to SEQ ID NO: 2.

DESCRIPTION

Figure 3A:
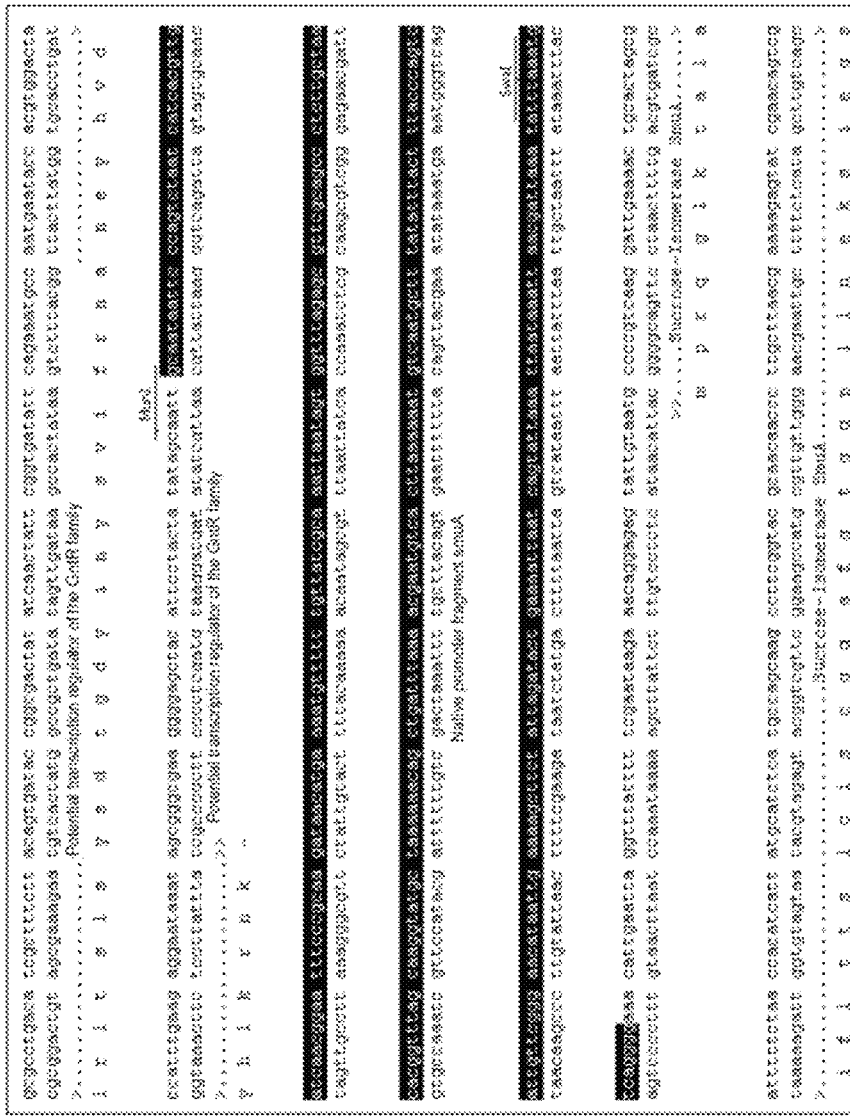
FIG. 3 shows DNA-sequence sections of the inter-genetic region between the newly discovered 3'-region of the gntR gene, which codes for a potential transcription regulator of the GntR-family, and the 5'-region of the sucrose mutase gene smuA from P. rubrum. This figure also illustrates the preferred strategy according to the invention for a scar-free insertion of homologue substitute promoters: A MunI interface is selected, located naturally approx. 35 bp downstream in reference to the putative gntR gene. Additionally, preferably an AAAC sequence is used, located immediately prior to the natural smuA ribosome bonding site (RBS), representing a part of the PmeI interface GTTT/AAAC (FIG. 3B). An episomal introduction of a MunI/PmeI-interim fragment (FIG. 3B) allows the targeted insertion of substitute promoters.
FIG. 3C shows as an example the scar-free insertion of the ribB promoter, here also called 3C1. Relevant sequences are emphasized in FIGS. 3A-C.

The invention relates to the biotechnological production of isomaltulose and isomaltulose-containing compositions and provides improved means for it, particularly microbial cells.

Disaccharide isomaltulose (palatinose) and trehalulose can be produced by rearranging (isomerisation) from sucrose (cane sugar, beet sugar). Sucrose-isomerisation products, particularly isomaltulose, are increasingly used as sucrose replacement products in food and similar products. Isomaltulose is an acrogenic sugar with a low glycemic index and has been licensed as a food or food additive since 2005. Additionally, isomaltulose or isomaltulose-containing compositions, which can be produced from sucrose, are source materials for the production of the sugar alcohol isomalt, a racemic mixture of 1,6-GPS (6-O-α-D-glucopyranosyl-D-sorbite) and 1,1-GPM (1-O-α-D-glucopyranosyl-D-mannite), as well as from deviations therefrom, particularly GPS- or GPM-enriched mixtures thereof. In the meantime, isomalt has been established as a sugar replacement in foods and similar products. The conversion of isomaltulose into isomalt and similar products occurs by catalytic hydration, as is commonly known, alternatively by biotechnological conversion.

The biotechnological production of isomaltulose and trehalulose is known to occur by enzymatic isomerisation of sucrose with the use of preferably immobilized bacteria cells or fragments thereof. The isomerisation occurs here via the activity of the bacterial enzyme sucrose mutase, E.C. 5.4.99.11 (synonyms: sucrose-isomerase, sucrose-mutase, sucrose-isomerase, isomaltulose-synthase). Microorganisms that are known to show sucrose-mutase activities and can be used in biotechnological processes are particularly *protaminobacter rubrum, erwinia rhapontici, pseudomonas mesoacidophila, pantoea dispersa,* and *serratia plymuthica.* Their sucrose-mutase is also known under the names of SmuA, Pal I, SmtA, MutB, SIM and others. The bacterial sucrose-mutases are coded by a chromosomal gene. The genetic expression is controlled via a sucrose-mutase promoter element. In the following the sucrose-mutases are uniformly called by the term "SmuA" of the sucrose-mutase of *P. rubrum*, without it here being restricted to the sucrose-mutase from *P. rubrum*. In *P. rubrum*, SmuA is coded by the chromosomal gene marked smuA; the expression is controlled via a smuA-promoter element. In the following, the name smuA also represents the sucrose-mutase genes of other organisms.

Genetically modified transgenic microorganisms are known from EP 0751218 A and WO 95/20047 A, which show sucrose mutase activity and in which by way of mutagenesis of the cell at least one gene, which codes the enzyme activity of the sucrose metabolism, is inactivated.

The rate of metabolizing the substrate sucrose into isomaltulose and perhaps additionally into trehalulose in known microorganisms needs improvement. Additionally, the sucrose mutase activity in known microorganisms is also dependent on the concentration or presence of sucrose in the culture medium, which complicates the biotechnological processing. Additionally, there are statutory restrictions and regulations for genetically modified organisms (GmO), for example the German Safety Regulation for Gene-technology (GenTSV). In addition to the provision of microorganisms with an improved yield of isomaltulose, it is also desired to obtain improved microorganisms not subject to statutory regulations.

The underlying technical problem to be attained by the invention comprises to provide improved methods and means, particularly improved microorganisms for the biotechnological production of isomaltulose and isomaltulose-containing compositions, which overcome the disadvantages known from prior art.

The invention attains this technological problem entirely by the provision of novel microbial cells, which in reference to the wild type of this cell, preferably otherwise unmodified, shows a formation rate of isomaltulose, i.e., a synthesis rate, increased by a factor of 2, preferably by a factor of 2.5, particularly preferred by a factor of 3 or 4 or 5 or more.

In this context, the invention preferably provides a cell comprising an elevated activity in reference to the wild type by at least a factor of 2, preferably by a factor of 2.5, particularly preferred by a factor of 3 or 4 or 5 or more, i.e., a particularly volume activity of sucrose mutase expressed by the cell. In a preferred embodiment the cell according to the invention shows in reference to its wild type an expression of sucrose mutase independent from the substrate, particularly from the concentration of sucrose.

In order to produce a cell according to the invention, the invention provides to substitute the non-coding promoter range of the gene smuA, which codes the sucrose mutase SmuA, by another strong, preferably internal endogen or homologue promoter or a functional promoter fragment thereof (=substitute promoter) of the preferably otherwise unmodified wild type of the cell. The inventors surprisingly found highly-effective homologue and particularly endogen, i.e., organism-internal promoters as well as fragments thereof, by which the expression of the smuA-gene and consequently particularly the concentration of the sucrose mutase in the periplasm of the cell and thus particularly the volume activity and here particularly the formation rate of isomaltulose can be increased in reference to the wild type of the cell.

The objective of the invention is therefore a cell, which comprises particularly a genome, preferably an endogen, sucrose mutase gene (smuA-Gene), which codes a sucrose mutase (SmuA), with a smuA-sucrose mutase-promoter element or promoter (smuA-promoter), i.e., at least one unit controlling or regulating the expression of this gene substituted by at least one other promoter or a fragment thereof (substitute promoter), with the substitute promoter being selected from: (a) an endogen promoter different from the smuA-promoter from the internal stem of the cell (internal, endogen promoter), (b) a promoter homologue in reference to the endogen promoter according to (a) from an external donor stem (external, homologue promoter), and (c) a functional promoter fragment of (a) or (b), particularly able to control or regulate the expression of this smuA-gene, particularly in reference to the wild type of the cell.

In a particularly preferred embodiment, this cell is a self-cloning stem, which was created by self-cloning using cell-internal (endogenous) gene sequences. The cell according to the invention therefore preferably represents a promoter-reorganization stem. Here, a stem with improved characteristics is created according to the invention via a copy of another, not protein-coding, preferably stem-internal (endogenous) regulatory fragment, i.e., promoter or its functional fragment, which is used by the promoter reorganization to express the internal sucrose mutase. Advantageously this promoter reorganization stem forms no new protein; it preferably only triggers the expression of greater amounts of cell-internal sucrose mutase SmuA, which is also expressed in an identical form by the wild type of the cell. Preferably, no external genes and/or gene fragments are included in the cell, and preferably no external coding and/or non-coding polynucleic acid molecules in the cell according to the invention, namely neither episomally nor chromosomally. It is understood that for the production of the self-cloning stem in this variant of the embodiment temporarily intermediate vector elements are inserted into the cell, which here are not lastingly manifested, but preferably are removed from the cell again, preferably by way of selection to the second recombination event according to the invention. The gene sequences are preferably substituted without scarring. The teaching according to the invention waives in this embodiment the lasting insertion of genetic material from an external "donor organism" according to GenTSV. This way, an improved microbial cell is provided, which according to applicable law and regulations is not considered a "genetically modified organism" (GMO). The compliance with safety regulations, restrictions for use, and conditions applicable for GMOs, is here not or not entirely mandatory, which facilitates particularly the economic utilization of the cell according to the invention.

In an alternative second embodiment the invention provides a recombinant cell, showing a homologue promoter. This cell carries at the position of the native smuA-promoter at least one other promoter, originating from a homologue donor organism or a functional promoter fragment thereof. This is preferably homologue in reference to the endogenous substitute promoter of the first embodiment of the invention.

In a preferred embodiment of the invention, the substitute promoter is selected or characterized by promoters of the group comprising:

Promoter of the gene of the 3,4-dihydroxy-2-butanon-4-phosphate synthase ribB,
Promoter of the gene ompA coding the "outer membrane protein,"
Promoter of the gene coding the "putative transcription activator ECA2934,"
Promoter of the gene of the ribonuclease E me,
Promoter of the operon of the 50S ribosomal L21-proteins,
Promoter of the operon of the cold-shock protein CspE,
Promoter of the operon of the 50S ribosomal L28-proteins, and
Promoter of the gene of the NAD dependent epimerase-dehydratase.

In a preferred variant, a functional promoter fragment of the entire promoter is provided as the substitute promoter, capable to control the expression of the smuA-gene according to the invention.

Tables 1A and 1B list preferred substitute promoters according to the invention and their characteristic sources.

TABLE 1A

| Size (bp) | Promoter fragment characterized in source; Homology for: | SEQ ID NO: |
|---|---|---|
| 321 | *P. rubrum* ribB promoter range (3,4-dihydroxy-2 butanone 4-phosphate synthase) | 2 |
| 313 | Promoter range ribB (3,4-dihydroxy-2 butanone 4-phosphate synthase, Spro_4286) from *Serratia proteamaculans* 568 Identities = 298/313 (95%) | 3 |
| 228 | *P. rubrum* ompA Promoter range | 4 |
| 180 | ompA Promoter from *S. proteamaculans* (Spro_1754) Identities = 178/180 (98%) | 5 |
| 178 | ompA Promoter from *S. marcescens* (emb X00618.1) Identities = 173/180 (96%) | 6 |
| 109 | *P. rubrum* inter-genetic range between "hypothetical protein ECA2934" and "putative transcriptional regulator" | 7 |
| 59 | Promoter range before "ECA2934 putative transcriptional regulator [*Pectobacterium atrosepticum* SCRI1043]" from *Erwinia carotovora* subsp. *atroseptica* SCRI1043 (emb BX950851.1) Identities = 51/59 (86%) | 8 |
| 209 | *P. rubrum* intergenetic range between "ribonuclease E" and "23S rRNA pseudouridylate synthase C"; promoter activity towards ribonuclease | 9 |
| 210 | intergenetic region between "ribonuclease E" (Spro_1898) and 23S rRNA pseudouridylate synthase C (Spro_1899) in *S. proteamaculans* (gb CP000826.1) Identities = 203/210 (96%) | 10 |
| 165 | Promoter range of the "ribonuclease E (rne)" Gene from *Serratia marcescens* (gb AF259269.1, AF259269) Identities = 158/165 (95%) | 11 |

TABLE 1B

| Size (bp) | Promoter fragment characterized in source; Homology for: | SEQ ID NO: |
|---|---|---|
| 242 | *P. rubrum* intergenetic range: flanking genes "Octaprenyl diphosphate Synthase" and "50S ribosomal protein L21" | 12 |
| 242 | Promoter region of the "50S ribosomal protein L21" (Spro_0473) from *S. proteamaculans* (gb CP000826.1) Identities = 236/242 (97%) | 13 |
| 120 | *P. rubrum* Promoter range of the "cold shock protein CspE" | 14 |
| 118 | Promoter region of the "cold shock protein CspE" (Spro_1189) from *S. proteamaculans* (gb CP000826.1) Identities = 111/118 (94%) | 15 |
| 115 | Promoter region of the "cold shock protein CspE" Identities = 94/115 (81%) | 16 |
| 238 | *P. rubrum* Promoter range "50S ribosomal protein L28" | 17 |
| 238 | Promoter region of the "50S ribosomal protein L28" (Spro_4481; gene "rpmB") from *S. proteamaculans* (gb CP000826.1) Identities = 231/238 (97%) | 18 |
| 238 | Range of the "waa gene clusters" from *S. marcescens* stem N28b (gb U52844.3 SMU52844) Identities = 226/238 (94%) | 19 |
| 152 | *P. rubrum* Promoter range "NAD dependent epimerase-dehydratase" | 20 |
| 86 | Promoter region of the "NAD dependent epimerase-dehydratase (Spro_2372)" from *S. proteamaculans* (gb CP000826.1) Identities = 73/86 (84%) | 21 |

The substitute fragment preferably used according to the invention, which originates from the promoter of the gene of the 3,4-dihydroxy-2-butanon-4-phosphate synthase ribB or a homologue region, is characterized in the nucleotide-sequence selected from: SEQ ID NO: 2 and SEQ ID NO: 3. In a preferred embodiment the cell is a *P. rubrum* cell, self-cloned with the substitute fragment according to SEQ ID NO: 2 from *P. rubrum*.

A substitute fragment preferably used according to the invention, which originates from the promoter for the "outer membrane protein" coding the gene ompA or a homologue region, is characterized in the nucleotide sequence selected from: SEQ ID NO: 4, SEQ ID NO: 5 and SEQ ID NO: 6. In a preferred embodiment the cell represents a *P. rubrum* cell, self-cloned with the substitute fragment according to SEQ ID NO: 4 from *P. rubrum*.

A substitute fragment preferably used according to the invention, which originates from the promoter of the gene of the putative transcription activators ECA2934 or a homologue region, is characterized in the nucleotide sequence selected from: SEQ ID NO: 7 and SEQ ID NO: 8. In a preferred embodiment, the cell is a *P. rubrum* cell, self-cloned with the substitute fragment according to SEQ ID NO: 7 from *P. rubrum*.

A substitute fragment preferably used according to the invention, which originates from the promoter of the gene of the ribonuclease E rne or a homologue region, is characterized in a nucleotide sequence selected from: SEQ ID NO: 9, SEQ ID NO: 10 and SEQ ID NO: 11. In a preferred embodiment the cell is a *P. rubrum* cell, which is self-cloned with the substitute fragment according to SEQ ID NO: 9 from *P. rubrum*.

A substitute fragment preferably used according to the invention, which originates from the promoter of the operon of the 50S ribosomal L21-protein or a homologue region, is characterized in the nucleotide sequence selected from: SEQ ID NO: 12 and SEQ ID NO: 13. In a preferred embodiment the cell is a *P. rubrum* cell, self-cloned with the substitute fragment according to SEQ ID NO: 12 from *P. rubrum*.

A substitute fragment preferably used according to the invention, originating from the promoter of the operon of the cold shock protein CspE or a homologue region, is characterized in the nucleotide sequence selected from: SEQ ID NO: 14, SEQ ID NO: 15, and SEQ ID NO: 16. In another preferred embodiment according to the invention the cell is a *P. rubrum* cell, which is self-cloned with the substitute fragment according to SEQ ID NO: 14 from *P. rubrum*.

A preferred substitute fragment used according to the invention originating in the promoter of the operon of the 50S ribosomal L28-proteins or a homologue region is characterized in the nucleotide sequence selected from: SEQ ID NO: 17, SEQ ID NO: 18, and SEQ ID NO: 19. In a preferred embodiment the cell is a *P. rubrum* cell, which is self-cloned with the substitute fragment according to SEQ ID NO: 17 from *P. rubrum*.

Finally, a preferred substitute fragment used according to the invention originating in the promoter of the gene of the NAD-dependent epimerase-dehydratase or a homologue region is characterized in the nucleotide sequence selected from: SEQ ID NO: 20 and SEQ ID NO: 21. In a preferred embodiment the cell is a *P. rubrum* cell, which is self-cloned with the substitute fragment according to SEQ ID NO: 20 from *P. rubrum*.

The endogen or alternatively homologue substitute promoter according to the invention is therefore characterized by a poly-nucleotide or preferably formed therefrom, which preferably includes or comprises a nucleotide sequence selected from the group of endogenous or homologue substitute sequences according to the invention comprising SEQ ID NO: 2 to SEQ ID NO: 21 and their functional modifications and fragments. Particularly this poly-nucleotide is used as the substitute promoter; alternatively preferred it comprises this poly-nucleotide as the essential or characterizing functional element. The invention therefore relates to functional fragments or modifications of these concretely mentioned poly-nucleotides, easily accessible for one trained in the art, when and to the extent they can act as promoters or as an element regulating the expression of the sucrose mutase gene smuA.

The invention preferably also relates to functional poly-nucleotide molecules with sequences homologue in reference thereto, which show at least 85%, preferably more than 90%, or more than 95%, or more than 97% sequence identity with the above-mentioned concretely named sequences. One trained in the art knows the experimental methods and algorithms to determine the sequence homology and the functional analogy.

A "functional fragment" is particularly considered a poly-nucleotide molecule with a sequence shortened in reference to the concretely named sequence, which includes and preferably comprises the actual promoter motif, i.e., the regulatory unit initiating the expression of the smuA-gene. One trained in the art knows suitable routine screening methods in order to determine suitable functional fragments in the sense of the invention. These easily determined functional fragments are also an objective of the present invention. Preferably the fragments are shortened in reference to the here concretely named nucleotide molecule by approximately 100 bp, 50 bp, 20 bp, 10 bp, 5 bp or 2 bp or by approximately 50, 20, 10, 5 or 2 of the original base number.

A "functional modification" of the poly-nucleotide molecule with the concretely named sequences is particularly understood to be a poly-nucleotide molecule acting as the regulatory unit, which can initiate the expression of the smuA-gene, which differs particularly directly by the substitution, deletion, or addition of one or more nucleotides from the concrete poly-nucleotide molecule. One trained in the art knows suitable screening methods in order to easily find such modified molecules which are suitable for implementing the invention. These modifications are deducted preferably by way of substitution, deletion and/or addition of 1 or more 2, 3, 4, 5, or about 10, 20, 50 or 100 or more nucleotides from the concretely named poly-nucleotide molecules.

These functional modifications or fragments originate in a preferred variant of the invention endogenously from the host cell, particularly preferred from its genome. In an alternative variant these modifications or fragments are homologue elements from other organisms.

Additionally, the invention also comprises poly-nucleotide molecules, suitable as regulatory units to initiate the expression of the smuA-gene in the cell and which can be used as a substitute promoter molecule according to the invention, which results from the randomized synthesis or modification of the above-mentioned substitute promoters in a manner known per se. It can be provided by one trained in the art using routine processes from the teaching described here in a manner known per se.

Preferably the substituted or "replaced" smuA-promoter element according to the invention is localized in a smuA-unit, namely preferably in the intergenetic region between the gene smuA and a here newly found, upstream located ORF. Here, a "smuA-unit" is considered the chromosomal organization upstream in reference to the smuA-gene with regulatory sequences in the 5'-UTR (promoter, operator) of the smuA-expression. In particular, the smuA-unit is characterized in the poly-nucleotide with the SEQ ID NO: 1 (FIG. 1); the FIGS. 3ABC illustrate the elements to be preferably substituted of the inter-genetic region of the smuA-unit of *P. rubrum*.

The invention preferably provides a host cell, selected from microorganisms of the groups of gamma-proteobacteria and the unclassified gamma-proteobacteria. Preferably the cell is selected from a group comprising microorganism of the types: *escherichia, salmonella, serratia, erwinia, enterobacter, klebsiella, rauoltella, pectobacterium, pseudomonas, azotobacter, pantoea, leucanea*, as well as *protaminobacter*. Particularly preferably, the cell is selected from the group comprising: *klebsiella* sp., particularly the stem LX3 and stem NK33-98-8, *klebsiella pneumoniae*, particularly the stem 342; *enterobacter* sp., particularly the stem SZ62; *enterobacter* sp., particularly the stem FMB1; *rauoltella planticola; pantoea dispersa; erwinia rhapontici; erwinia tasmaniensis*, particularly the stem Et1/99; *pectobacterium atrosepticum*, particularly the stem SCRI 1043; *pectobacterium carovotum*, particularly the sub-species *brasiliensis*, particularly the stem PBR 1692; *protaminobacter rubrum; pseudomonas mesoacidophila; serratia plymuthica* as well as *azotobacter vinelandii* and *leucanea leucocephalia*. In a particularly preferred variant the cell *protaminobacter rubrum* (*P. rubrum*) or a biotechnologically modified stem thereof may be used. It shall be understood that the invention also extends to immobilized and/or otherwise modified forms of these host cells, which may be particularly suitable for the biotechnological process.

The objective of the invention also includes means to produce a cell according to the invention, particularly a self-cloning stem. One such means is a poly-nucleotide molecule, preferably present in an isolated form already described in greater detail per se, including or comprising the above-characterized substitute promoter or a functional fragment thereof, which is capable of regulating the expression of the smuA-gene.

The objective of the invention is also a vector or a vector system, particularly a substitute plasmid, suitable to insert the poly-nucleotide molecule, described above in greater detail, according to the invention, i.e., the substitute promoter or a fragment of a substitute promoter. The host cell is preferably one of the above-characterized micro-organisms. Preferably the vector serves to integrate the substitute promoter or the fragment of the substitute promoter in the chromosomal genome of the cell, particularly to substitute the native promoter of the smuA-gene in the chromosomes of the cell, in order to this way create particularly a self-cloning stem.

The substitute vector initiating the promoter substitution is preferably designed such that it does not reproduce in the host cell into which it has been introduced. A preferred vector construct is a pUT-derivative, which is based on an R6K replication source; this vector abstains from reproducing particularly in *P. rubrum*, at least conditionally.

The objective of the invention is also a method for producing a cell according to the invention to convert sucrose into isomaltulose or isomaltulose-compositions, with the method comprising at least the following steps: In a first step, a wild type stem or an already modified—classically or by way of recombination—stem of a cell is produced; in a second step this stem is made to contact or connect to at least one of the above-characterized poly-nucleotide molecules according to the invention, here particularly the substitute promoter or the fragment of the substitute promoter and/or at least one of the above-characterized vectors, comprising the substitute promoter or the fragment of the substitute promoter, namely preferably such that the substitute promoter or the substitute plasmid is inserted into the cell. A preferred method is the inter-generic conjugation with particularly *E. coli* as the donor stem.

In a preferred other, preferably directly subsequent step, the cell is cultivated under conditions allowing a homologue recombination of the inserted poly-nucleotide molecule or the vector or substitute plasmid the poly-nucleotide molecule carrying the poly-nucleotide molecule and the respective region in the genome of the cell such that the substitute promoter is integrated in the genome of the cell. In a preferred embodiment, the vector or the substitute plasmid no longer comprising the originally contained substitute promoter, and preferably comprising the substituted smuA-promoter, is eliminated by the selection of the second recombination event.

According to a second aspect of the invention, cells are the objective of the invention in which the smuA-gene, particularly under the regulation of at least one of the above-characterized substitute promoters or a functional fragment of the substitute promoter, alternatively or preferably additionally is expressed extra-chromosomally (episomally), as well as means for the production of such cells. One such means is another poly-nucleotide molecule, which includes a coding section that can express sucrose mutase in at least one or several copies and additionally shows at least one other element regulating the expression of this sucrose mutase in at least one or several copies, thus particularly a promoter element. The element regulating the expression of the sucrose mutase gene is selected from the group of the above-characterized substitute promoters according to the invention and functional fragments thereof. The objective of the invention is therefore a sucrose mutase-expression magazine.

In an alternative variant of this aspect of the invention the poly-nucleotide molecule according to the invention, particularly the expression magazine, is present in an isolated form. For example, it can be transferred into a host cell in a manner known per se. Further, it is provided to use the poly-nucleotide molecule, particularly the expression magazine, to develop cell-free systems and biocatalysts.

The objective of this second aspect of the invention is also a vector, particularly an expression vector, which comprises at least one copy of the above-characterized poly-nucleotide molecule, particularly the expression magazine, in the preferred form that can be expressed. The expression vector may preferably be inserted into a host cell in order to express the sucrose mutase gene (smuA), preferably episomally. In a preferred alternative variant the vector according to the invention serves to insert the sucrose mutase-expression magazine into the chromosomal genome of the host cell.

The objective of the second aspect of the invention is also a method for the production of a cell according to the invention capable to recombine in order to convert sucrose into isomaltulose or isomaltulose-compositions, with the method comprising at least the following steps: In a first step a wild type stem of the cell is provided; in a second step this stem is brought into contact with at least one of the above-characterized poly-nucleotide molecules according to the invention, particularly the sucrose mutase-expression magazine, and/or at least one of the above-characterized vectors, particularly the sucrose mutase-expression vector. Preferably here the poly-nucleotide molecule and/or the vector are integrated in the cell in a form that can be expressed.

The invention also relates to the use of the above-characterized poly-nucleotide molecules according to the invention, substitute promoters, and their fragments, or complete sucrose mutase-expression magazines, for the production of a cell according to the invention; according to the first aspect of the invention therefore a self-cloning stem, according to the second aspect of the invention therefore a recombinant cell.

The invention also relates to the use of the above-characterized vector, according to the first aspect of the invention therefore a substitute plasmid, according to the second aspect of the invention therefore an expression vector for the production of such a cell.

The invention finally relates also to a method for the biotechnological production of isomaltulose and/or an isomaltulose-containing/trehalulose-containing composition, particularly an isomaltulose-composition, preferably comprising the substrate sucrose or a sucrose-containing substrate. According to the invention the method comprises at least one step: Cultivating the cell according to the invention in a culture medium containing the substrate, namely under conditions allowing a conversion of the substrate into isomaltulose, preferably under the use of cell-internal, homologue sucrose mutase (SmuA). Preferably, in a preferred subsequent step, the isomaltulose or the isomaltulose-composition is isolated from the culture medium and/or the cell.

The expression of sucrose mutase in the host cells according to the invention is beneficially independent or largely independent from the sucrose concentration, and the invention allows the growth of host cells according to the invention, i.e., the creation of biomass, in a glucose medium (C-source).

In the context of the invention, "isomaltulose-composition" relates to the isomerisation product of sucrose. This substance overwhelmingly includes isomaltulose. Additional components are trehalulose and isomelezitose. This particularly relates to the following composition: 70 to 90% isomaltulose, 5 to 10% trehalulose, 0 to 0.5% isomelezitose, 0 to 0.2% trisaccharide and 0 to 0.2% residual sucrose.

Accordingly it is an objective of the invention to use the above-characterized cell according to the invention for the biotechnological production of isomaltulose or an isomaltulose-composition, preferably comprising sucrose or a sucrose-containing substrate, and preferably produced according to the method described here.

The invention is explained in greater detail using the following examples, without being restricted thereto:

The sequence protocol includes:

SEQ ID No:1: DNA-sequence upstream in reference to the smuA-gene, comprising the native smuA-promoter/operator, which can be substituted entirely or partially by the substitute promoter according to the invention or its functional substitute promoter fragment;

SEQ ID No:2 to 21: Sequences of functional substitute promoters, which can regulate the expression of the smuA-gene in the cell instead of the native smuA-promoters.

In order to substitute the identified strong promoters for the native smuA-promoter, according to the invention preferably a substitution occurs, which is performed without the introduction of novel, non-homologue sequences into the organism. For this purpose, according to the invention preferably the following process occurs essentially: A promoter substitute plasmid is created, which preferably comprises approx. 1000 bp of a DNA-region upstream and downstream of the smuA-promoters. Subsequently a non-scarring substitution of the native smuA-promoter occurs, located in the plasmid and showing a size of approx. 400 bp, for another homologue promoter. The base-equivalent substitution may be confirmed, for example by DNA-sequencing. The promoter substitute plasmid obtained in this way is transferred into the organism and the plasmid is chromosomally integrated via homologue recombination into the smuA-unit. The substitution of promoters preferably occurs by the simultaneous elimination of the substitute plasmid by a targeted selection of the second recombination event.

If applicable, the correct, non-scarring promoter substitution and the absence of any external sequences in the organism can be verified by PCR-methods and/or sequencing methods in a manner known per se. Additional securing is possible by southern-hybridization.

In order to substitute the native smuA-promoter, preferably the inter-genetic region between a potential regulator of the expression of the region coding the sucrose mutase and a region coding the sucrose mutase SmuA is selected on the chromosome of the bacteria. Particularly preferred, the interim fragment is removed by way of hydrolysis at the regions MunI and PmeI. Preferably the targeted insertion of the homologue substitute promoter, preferred according to the invention, occurs as a MunI or EcoRI/PmeI-fragment.

EXAMPLE 1

Substitution of the smuA-Promoters by Self-Cloning in P. rubrum

All cloning and DNA-modifications are performed as described in Sambrook et al., 1989 (Molecular cloning: A laboratory manual, 2nd ed. Cold Spring Harbor Laboratory, Cold Spring Harbor, N.Y.). PCR-charges, kits for the isolation of nucleic acids, detection and selection methods, and cultivation were performed in a manner known per se, unless stipulated otherwise, according to the specifications of the respective manufacturers.

1.1 Homologue P. Rubrum promoters

Chromosomal DNA of the P. rubrum wild type is isolated and partially metabolized with AluI. The fragments are cloned into the StuI interfaces by two different promoter probe-vectors shown in FIG. 2, which essentially differ in their number of copies: While the vector pUCTT-gusA shows a pUC-derivative with a high number of copies and carrying the chloroamphenicol-resistant gene cat of pBR328 (DSMZ, Brunswick), the vector pSCTT-gusA is a vector with a low number of copies, deducted from the known plasmid pSC101 (DSMZ, Brunswick) and carrying the canamycin-resistant gene aphII. In both vectors the gusA-gene is used as the promoter-reporting gene, which is coded for a β-glucuronidase and expressed after the insertion of a functional promoter fragment.

After the addition of the substrate 5-bromo-4-chloro-3-indolyl-β-D-glucuronic acid (X-Gluc) a successful expression can be detected by blue coloration (execution according to Platteeuw C. et al., 1994, Appl Environ Microbiol. 60:587-93). The three terminators (Ter) can prevent any undesired expression of the reporter gene by potential, plasmid-internal promoter elements. Both vector types replicate in E. coli as well as in P. rubrum.

In order to control the promoter function of the host cell-internal substitute promoter fragments, the chromosomal β-glucuronidase gene uidA, naturally present in E. Coli, can be deactivated by one trained in the art using methods known to him/her, in order to create an E. coli gusA-test stem E. coli DH10BΔuidA.

The transformation of pUCTT-gusA or pSCTT-gusA-gene bank of the substitute promoters in E. coli DH10BΔuidA leads to blue colonies, in which the promoter-less gusA-reporter gene is expressed by the substitute promoter fragment cloned in.

The restriction analysis of plasmid-DNA, isolated from blue colonies, shows that differently sized chromosomal P. rubrum fragments also have promoter functions.

Using the electroporation (preparation of electro-competent cells and execution according to Dower et al., 1988, Nucleic Acids Res., 16:6127-6145) the clones can be transferred to P. rubrum and the promoter activity, already detected in E. coli, can be confirmed.

1.2 Non-scarring insertion of substitute promoters

The substitute promoters according to the invention (SEQ ID NO: 2 to 21) are each substituted in a non-scarring fashion for the native chromosomal smuA-promoter/operator range (cf. SEQ ID NO: 1 and FIG. 3ABC), by way of homologue recombination.

This approach is based on the chromosomal integration of a promoter substitute plasmid by way of homologue recombination. A base vector is provided, not reproducing in P. rubrum, at least conditionally. As an example, pUT-derivatives are inserted based on a R6K replication origin (Herrero et al., 1990, J. Bacteriol., 172:6557-67). These vectors reproduce only when the coding pir-gene essential for the replication of π-protein is present. Such a stem is E. coli S17-1λpir (Herrero et al., 1990, J. Bacteriol., 172:6557-67); it is used to construct the respective promoter substitute plasmids.

Figure 3B:
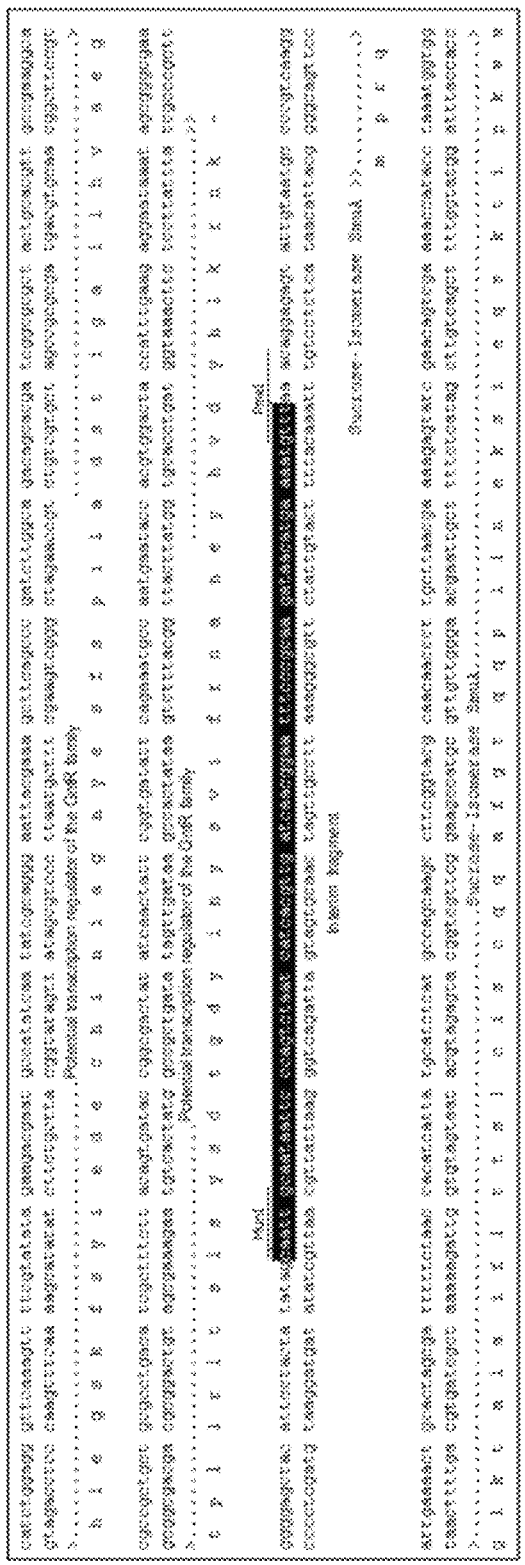
Figure 3C:
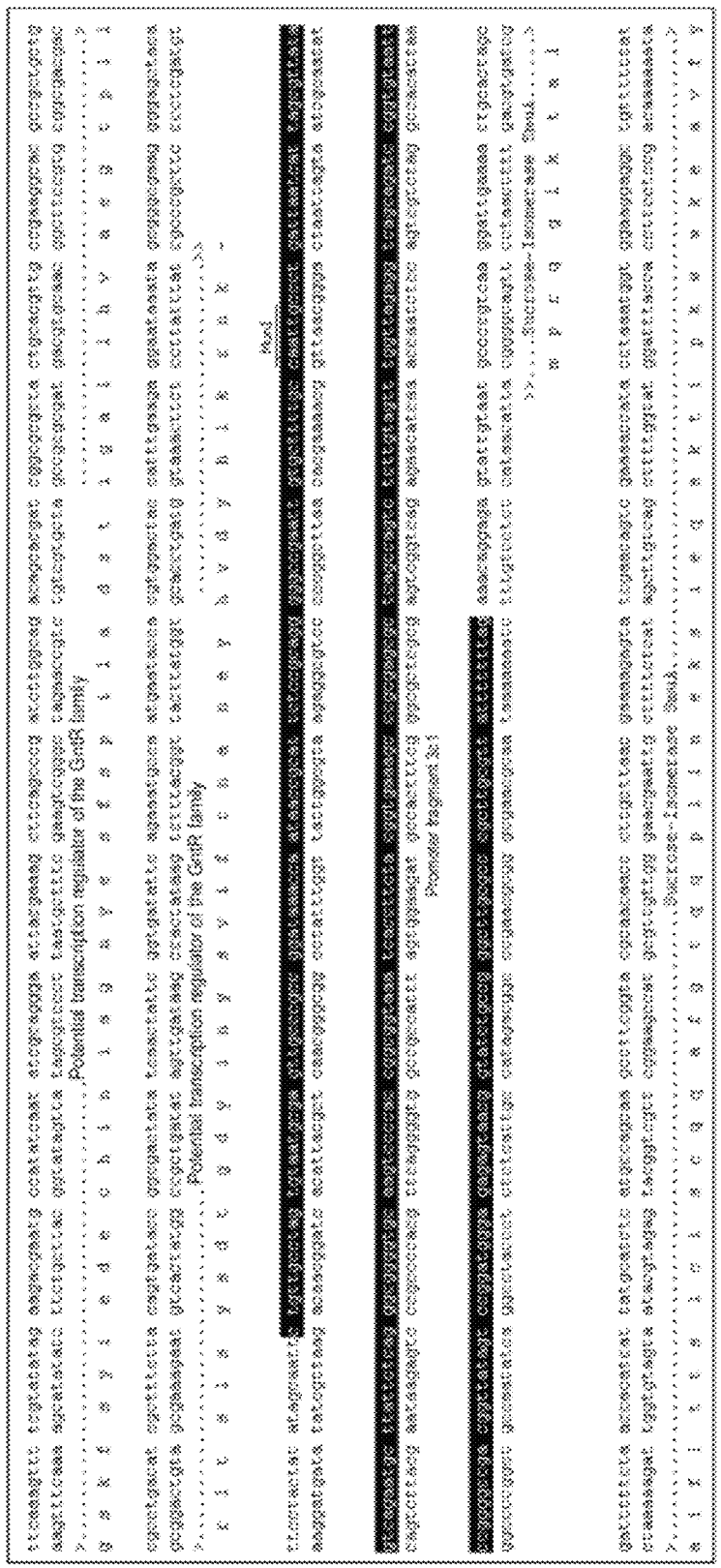

All promoter substitute plasmids according to the invention based on pUT-vectors are constructed such that the new promoter fragment to be substituted is flanked in a non-scarring fashion upstream by a 925 bp sized DNA fragment, coding the gntR-regulator, and downstream by a 1066 by sized DNA fragment, coding the 5' region of smuA. FIG. 3 shows in detail the realization of the cloning strategy, as an example for the ribB-promoter being the substitute promoter fragment (3C1). An exemplary, final promoter substitute plasmid (pUT-GntR-Pr3C1-SmuA'), triggering the substitution of the fragment 3C1 for the smuA-promoter, is shown in FIG. 4.

1.3 Creating promoter reorganization stems

The transfer of the promoter substitute plasmids to form P. rubrum is preferably realized by an inter-generic conjugation between E. coli S17-1λpir and P. rubrum. The pUT-plasmids used carry an "Origin of Transfer" (oriT) of the RP4 plasmid and can be mobilized by the RP4 plasmid chromosomally integrated in the E. coli S17-λpir to P. rubrum (Herrero et al., 1990, J. Bacteriol., 172:6557-67).

The conditions of the inter-generic conjugation have been optimized as follows: The selection of potential P. rubrum transconjugants requires a plasmid marker that can be selected in P. rubrum (e.g., aphII, canamycin-resistant), and a possibility to selectively inhibit the E. coli donor. By way of plating on a rifamycin-containing medium (100 µg/ml), spontaneously rifamycin-resistant P. rubrum wild type colonies are generated (P. rubrum Rif), which show no other differences from the wild type. The conjugation is performed as follows:

E. coli S17-λpir donor stems carrying the respective promoter substitute plasmid are drawn out over night in 5 ml dYT medium (per 1 liter: 16 g bacto trypton, 10 g bacto yeast extract, and 5 g NaCl) with canamycin (50 µg/ml) added at 37° C. The recipient P. rubrum was also drawn out over night in 5 ml dYT under the addition of rifamycin (100 µg/ml) at 30° C. 1 ml each of the overnight culture was injected into a conical flask with 100 ml dYT-medium (for additions, see above) and incubated at 30° C. (P. rubrum) or 37° C. (E. coli) and 250 rpm up to OD (600 nm) from 0.4 to 0.8. The donor and the recipient are mixed at a ratio of 1:4, centrifuged, washed with 1 ml dYT, and finally accepted in 100 µl dYT-medium. The suspension is applied by pipettes on a nitrocellulose filter (0.45 µm pore size) located on a dYT plate and incubated over night at 30°. The cells are then rinsed off the filter with 1 ml dYT, diluted, and plated on selection plates (dYT+canamycin 50 µg/ml and rifamycin 100 µg/ml) and incubated over night at 30° C.

Figure 5:
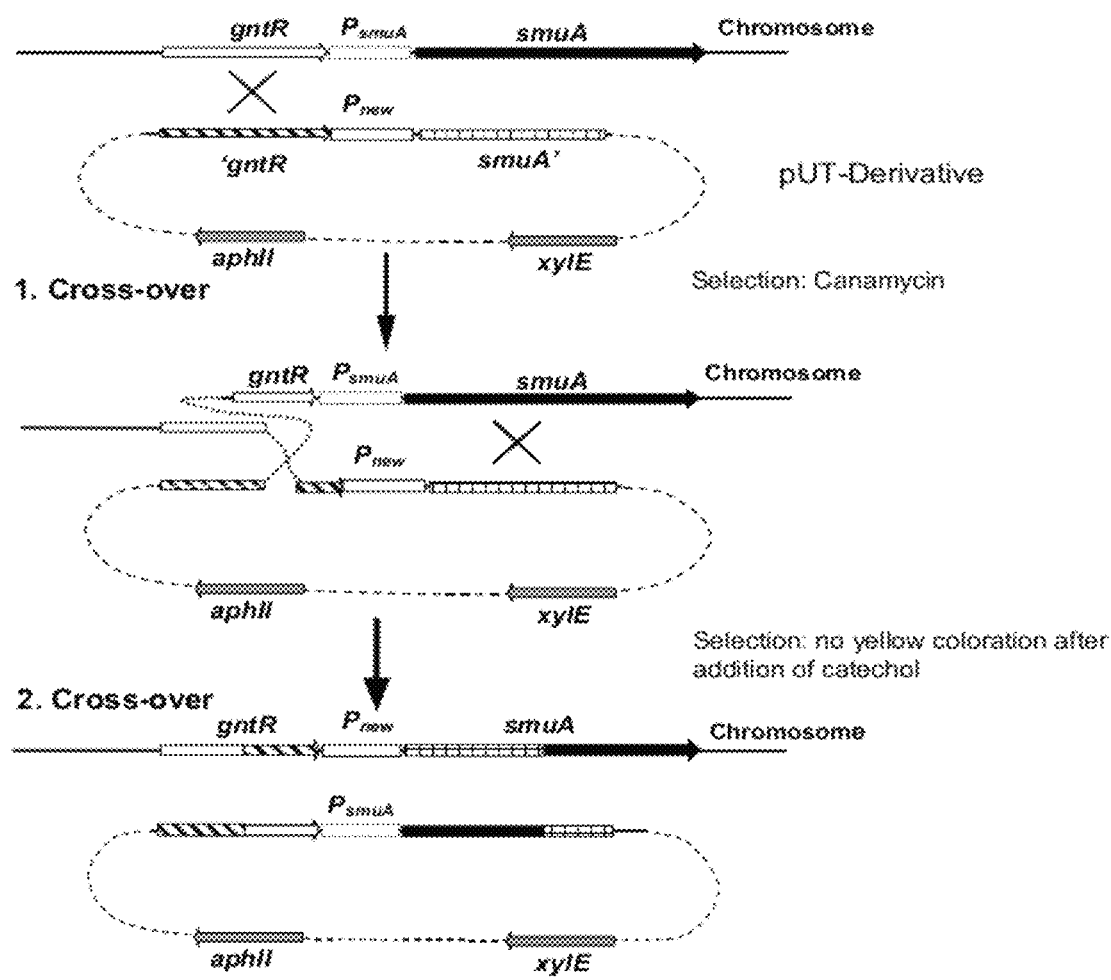
FIG. 5 illustrates schematically and as an example the process according to the invention to produce the organisms according to the invention: Substitution of the native smuA-promoter region by a homologue promoter by way of self-cloning. Based on a preferably non-replicating vector (e.g., pUT-vector) in the host cell P. rubrum preferably a promoter substitute plasmid is constructed in E. coli, containing the promoter to be substituted. It is coded upstream and without scarring by an approx. 1000 by sized DNA-fragment, which codes the putative gntR-regulator, and downstream it is flanked by an approx. 1000 by sized DNA-fragment of the SmuA-region, coding the 5' region of smuA. The plasmid created is transferred into the host cell, here: P. rubrum wild type. By selection on preferably kanamycin such colonies are selected therefrom which carry the substitute plasmids in the chromosome, preferably integrated in the chromosome by at least one of the two homologue regions. The incubation on kanamycin-free media allows the selection of promoter substitute stems, in which the integrated plasmid is disintegrated again via a second cross-over (second recombination event) from the chromosome. Such colonies are preferably provable phenotypically (no yellow coloring) by the absence of xylE-activity after the addition of catechol in a manner known per se. The successful production of the promoter reorganization stem can then be tested by molecular-biological methods (e.g., PCR) in a manner known per se, in order to additionally allow excluding the complete disintegration of the substitute plasmid, leading to the reconstruction of the wild type.

By the canamycin selection, such P. rubrum transconjugants are yielded, in which the plasmids are preferably integrated in the chromosome via one of the two homologue regions (FIG. 5). The incubation of canamycin-free medium allows the selection of promoter substitute stems, in which the integrated plasmid is disintegrated from the chromosome by a second cross-over. In order to prove the successful disintegration, color markers xylE can be inserted on a substitute plasmid. The xylE-gene codes for a catechol-2,3 dioxygenase, converting the catechol to 2-hydroxymuconic acid semialdehyde, which can be detected phenotypically by a striking yellow coloring. The disintegration of the previously integrated substitute plasmid is a rare occasion (1 of 1000 colonies) and can be detected by these markers via the designed clones not showing the yellow coloration after the addition of catechol (spray reagent: 0.2 ml of a 0.5 mol/l aqueous solution). Due to the fact that the disintegration of the substitute plasmid can also lead to the reconstitution of the wild type, all generated promoter reorganization stems can be tested and verified by PCR-experiments, southern-blot analyses, and genomic sequencing. The results show that the new stems generated developed free from scarring by base-identical substitution (self-cloning) and show no external sequences.

EXAMPLE 2

Product spectrum and synthesis performance 2.1 Analysis of the carbohydrate composition using HPLC The determination of the separated carbohydrates occurred via HPLC using the following components: HPLC pump; sample provider; RI (diffraction index)-detector; pre-column: 10 mm×4.6 mm, amino-phase (e.g., Zorbax-NH2); separating column: 250 mm×4.6 mm, amino-phase (e.g., Zorbax-NH2); interface, computer, and software to record and process measurements.

The measurement was performed under the following chromatographic conditions: injection volume: 10 µl; flow rate: 1.0 to 1.8 ml/min. The flow rate to be adjusted for optimal separation depends on the type and condition of the separating column as well as the composition of the eluent. For additional analysis parameters see Table 2.

TABLE 2

| Device: | HP1100 HPLC-System | |
|---|---|---|
| Column(s): | Zorbax-NH2 250 × 4.6 mm, 5 µm with pre-column 10 × 4.6 mm | at room temp. |
| Detector: | Detector of diffraction index | Heated to 30° C. |
| Eluent: | Acetonitrile 73% (v/v) | flux: 1.400 ml/min |
| Injection volume: | 10 µL | |
| Analysis period: | 30 min | |
| Sample concentration | 10% conc. sample solution | |

2.2 Whole-cell bio-transformation in the shaking flask

The growth of stems according to the invention and wild type-control stems occurred in 30 ml LB-medium (Start-$OD_{600}$ of 0.05). The cultures are each incubated at 30° C., 200 rpm in a horizontal shaking flask. After initially 24 hours of fermentation, 5×OD cells are removed, centrifuged, and washed with 1 ml Ca-acetate buffer (0.01 mol/l, pH 5.5). The cell pellets (equivalent to 5×OD cells) are each re-suspended in 1.25 ml Ca-acetate buffer (0.01 mol/l, pH 5.5) with a sucrose solution of 0.584 mol/l (200 g/l). The charges were incubated for biotransformation in deep-well plates under slight shaking at room temperature for 90 min. The reaction was stopped by heat treatment (5 min 98° C.).

TABLE 3

| SAMPLE ID | Fructose HPLC-NH2 g/L | Glucose HPLC-NH2 g/L | Saccharose HPLC-NH2 g/L | Isomaltulose HPLC-NH2 g/L | Trehalu. HPLC-NH2 g/L | Isomaltose HPLC-NH2 g/L | DP-3 HPLC-NH2 g/L | Isomelezitose HPLC-NH2 g/L | Remainder HPLC-NH2 g/L |
|---|---|---|---|---|---|---|---|---|---|
| 3C1A2S | 4.7 | 4.0 | 63.1 | 138.4 | 10.6 | 0.4 | <0.1 | 0.3 | 0.1 |
| 3C1B2S | 4.6 | 4.0 | 58.2 | 134.1 | 10.2 | 0.4 | <0.1 | 0.3 | <0.1 |
| WT2S | 1.6 | 1.4 | 166.1 | 42.6 | 3.4 | <0.1 | <0.1 | 0.1 | <0.1 |
| 3C1A2G | 4.0 | 3.5 | 78.2 | 111.6 | 8.9 | 0.1 | <0.1 | 0.1 | <0.1 |
| 3C1B2G | 3.8 | 3.3 | 79.0 | 108.4 | 8.4 | 0.2 | <0.1 | 0.1 | <0.1 |
| WT2G | 0.1 | 0.1 | 196.5 | 2.6 | 0.1 | <0.1 | <0.1 | <0.1 | <0.1 |
|  | Norm % | Norm % | Norm % | Norm % | Norm % | Norm % | Norm % | Norm % | Norm % |
| 3C1A2S | 2.1 | 1.8 | 28.5 | 62.4 | 4.8 | 0.2 | <0.1 | 0.2 | <0.1 |
| 3C1B2S | 2.2 | 1.9 | 27.5 | 63.3 | 4.8 | 0.2 | <0.1 | 0.1 | <0.1 |
| WT2S | 0.8 | 0.6 | 77.1 | 19.8 | 1.6 | <0.1 | <0.1 | 0.1 | <0.1 |
| 3C1A2G | 1.9 | 1.7 | 37.9 | 54.0 | 4.3 | 0.1 | <0.1 | 0.1 | <0.1 |
| 3C1B2G | 1.9 | 1.6 | 38.9 | 53.3 | 4.2 | 0.1 | <0.1 | <0.1 | <0.1 |
| WT2G | 0.1 | 0.1 | 98.4 | 1.3 | 0.1 | <0.1 | <0.1 | <0.1 | <0.1 |

Table 3 shows the results of the HPLC-analysis of the residue after fermentation under sucrose growth (S) or under glucose growth (G) with two individually created promoter substitute stems (No. 3C1A and No. 3C1 B) in reference to the wild type (WT):

The isomaltose amount of the 3C1 stems (3C1A2S and 3C1B2S) created under sucrose growth (S) is elevated in reference to the respective wild type (WT2S) by approx. the factor of 3.2.

Under glucose growth (G) the difference is more distinct because under these conditions SmuA is expressed in the wild type (WT2G) only in small amounts. The stems according to the invention (3C1A2G, 3C1B2G) produce only approx. 10% less isomaltulose compared to the sucrose growth.

During the further progression of the fermentation (more than 24 hours) isomaltulose is yielded by 70 to 90% and perhaps more than 90%.

2.3 Whole-Cell biotransformation in the fermenter

Wild type *P. rubrum* Z12 and the substitute stems of *P. rubrum* created by way of self-cloning were cultivated in the same medium. The growth of the pre-culture occurred in the shaking flask at 30° C. under aerobic conditions.

Comparing fermentations were performed with 500 ml fermenters (company Sixfors): culture medium: Soy peptone: 15.0 g; molasses (80° Bx): 20.0 g; $(NH_4)_2HPO_4$: 2.0 g; sucrose: 40.0 g; $H_2O$ ad 1000 ml, pH 7.2-7.4; fermentation parameter: ventilation rate (start of fermentation): 0.5 VVm; rotation of agitator: 500 rpm; $pO_2$: 20%

The fermenter was injected with 5 ml of a pre-culture in an exponential growth phase. The fermentation in the 500 ml-fermenters occurs under the above-mentioned parameters at 30° C. for 15 hours. After the end of the fermentations the cells were centrifuged for 30 min at 17,600×g and the clear residue is discarded. Subsequently the cell yield (dry bio mass) and its sucrose mutase activity were determined.

The dry biomass was determined by way of filtration of 10 ml fermentation suspension with a 0.45 μm filter and dehydration of this filter at 105° C. Two fermentations per stem were performed each.

The wild type yielded, after fermentation for 15 hours, a dry biomass of 85.1±5.6 g/kg and exemplarily the promoter substitute stem No. 3C1 yielded 80.9±1.0 g/kg. Based on this data no significant difference could be observed in the yield of dry biomass.

In order to determine the sucrose mutase activity 1 g moist biomass (BFM) each of the wild type and the self-cloned stems according to the invention were suspended in 50 g 10 mmol/l Ca-acetate buffer, pH 5.5 each, comprising 40% [w/v] sucrose. The cell suspension was incubated for 24 hours at 25° C. under shaking and samples were taken at different times. They were examined via HPLC for residual sucrose, isomaltulose, trehalulose, glucose, and fructose.

Figure 6:
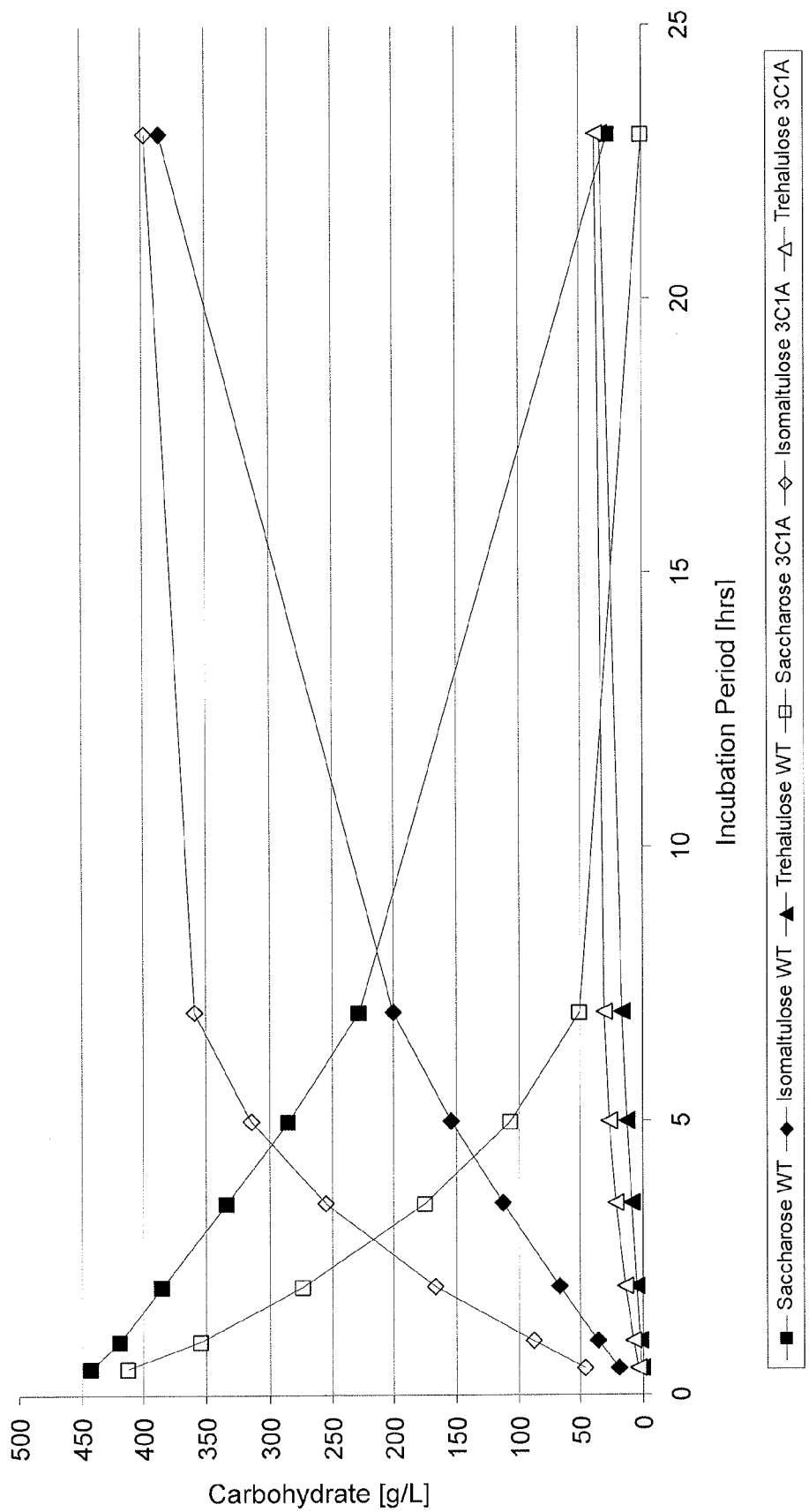
FIG. 6 shows the progression of the carbohydrate metabolism over 24 hours in the organisms according to the invention (No. 3C1A) and in comparison of to the wild type (WT).

FIG. 6 shows analysis data of the formation of isomaltulose from a 40% conc. sucrose in 10 mmol/l Ca-acetate buffer, pH 5.5. Samples were taken at different times and examined for the composition of the carbohydrates. The figure shows the conversion of 40% conc. sucrose into isomaltulose by the sucrose mutase of the wild type (WT) in reference to the exemplarily selected promoter substitute stem No. 3C1A. After 5 hours of incubation, using the sucrose mutase of the wild type 150 g isomaltulose, with the promoter substitute stem No. 3C1A, 320 g isomaltulose could already be proven, though.

Based on the conversion kinetics, the following specific activities could be calculated: Activity of the wild type: 1020±17.8 units/g dry biomass; activity of the stems (No. 3C1A and No. 3C1B): 3118±86.2 units/g dry biomass. The sucrose mutase activity was elevated in the substitute stems according to the invention in reference to the wild type by a factor of approximately 3.

The invention claimed is:

1. An isolated polynucleotide molecule, comprising a ribB promoter (a promoter of a 3,4-dihydroxy-2 butanone 4-phosphate synthase gene), or functional promoter fragment thereof, operably linked to a polynucleotide encoding a sucrose mutase SmuA.

2. A vector comprising one or more polynucleotide molecules according to claim 1.

3. An isolated microbial cell comprising the polynucleotide molecule of claim 1.

4. The isolated microbial cell according to claim 3, comprising the polynucleotide molecule integrated into a chromosome of the cell.

5. The isolated microbial cell according to claim 3, extra-chromosomally comprising the polynucleotide molecule.

6. A method for the production of a cell, comprising the steps:
  providing a wild type microbial cell and
  contacting the cell with a polynucleotide of claim 1.

7. A method for the biotechnological production of isomaltulose or an isomaltulose-composition comprising a sucrose-substrate, the method comprising: Cultivating the cell of claim 3 in a culture medium comprising the substrate under conditions allowing a conversion of the substrate to isomaltulose or an isomaltulose-composition.

8. The method according to claim 7, further comprising: isolating the isomaltulose or isomaltulose-composition.

9. The isolated polynucleotide molecule of claim 1, wherein the ribB promoter comprises SEQ ID NO: 2 or 3, or a functional promoter fragment thereof.

10. The vector of claim 2, wherein the ribB promoter comprises SEQ ID NO: 2 or 3, or a functional promoter fragment thereof.

11. The isolated microbial cell of claim 3, wherein the ribB promoter comprises SEQ ID NO: 2 or 3, or a functional promoter fragment thereof.

12. The isolated microbial cell of claim 3, wherein the ribB promoter is localized in an intergenic region between SmuA and an upstream located open reading frame (ORF).

13. The isolated microbial cell of claim 3, wherein the microbial cell is a micro-organism of a genus selected from the group consisting of *Escherichia, Salmonella, Serratia, Erwinia, Enterobacter, Klebsiella, Rauoltella, Pectobacterium, Pseudomonas, Azotobacter, Pantoea, Leucanea*, and *Protaminobacter*.

14. The isolated microbial cell of claim 13, wherein the microbial cell is of the species *Protaminobacter rubrum*.

* * * * *